US008449839B2

(12) United States Patent
Rajagopal et al.

(10) Patent No.: US 8,449,839 B2
(45) Date of Patent: May 28, 2013

(54) LIQUID WASTE MANAGEMENT SYSTEM

(75) Inventors: Ganesh Rajagopal, Carrollton, TX (US); James W. Whitt, Valley View, TX (US); GeDon G. Berryman, Fort Worth, TX (US); Daniel H. Lains, Coppell, TX (US); Brian L. Ochranek, Southlake, TX (US); Gregory A. Blackwell, Dallas, TX (US); Robert P. Luoma, II, Colleyville, TX (US); Jack F. Ramsey, Highland Village, TX (US)

(73) Assignee: Abbott Laboratories, Abbott Park, IL (US)

( * ) Notice: Subject to any disclaimer, the term of this patent is extended or adjusted under 35 U.S.C. 154(b) by 557 days.

(21) Appl. No.: 11/644,086

(22) Filed: Dec. 22, 2006

(65) Prior Publication Data
US 2008/0154543 A1    Jun. 26, 2008

(51) Int. Cl.
B01L 3/02         (2006.01)

(52) U.S. Cl.
USPC .............. 422/509; 422/63; 422/500; 422/501

(58) Field of Classification Search
USPC ............ 422/50, 68.1–82.13, 99, 63, 67, 100, 422/104, 62, 102, 105, 106, 112, 116, 500, 422/501, 509, 510; 73/61.56, 64.56; 700/266, 700/275, 281–283, 78, 80
See application file for complete search history.

(56) References Cited

U.S. PATENT DOCUMENTS

| | | | |
|---|---|---|---|
| 3,681,995 A | 8/1972 | Paatzsch | |
| 4,140,018 A | 2/1979 | Maldarelli et al. | |
| 4,259,288 A | 3/1981 | Welch | |
| 4,338,279 A | 7/1982 | Orimo et al. | |
| 4,517,160 A | 5/1985 | Galle et al. | |
| 4,558,946 A | 12/1985 | Galle et al. | |
| 4,634,576 A | 1/1987 | Galle et al. | |
| 4,781,891 A | 11/1988 | Galle et al. | |
| 4,844,887 A | 7/1989 | Galle et al. | |
| 5,147,610 A | 9/1992 | Watanabe et al. | |
| 5,201,232 A | 4/1993 | Uffenheimer | |

(Continued)

FOREIGN PATENT DOCUMENTS

| | | |
|---|---|---|
| EP | 0355823 A2 | 2/1990 |
| EP | 0 452 308 B1 | 10/1991 |

(Continued)

OTHER PUBLICATIONS

European Patent Office, International Search Report, Apr. 15, 2008.

(Continued)

*Primary Examiner* — Jill Warden
*Assistant Examiner* — Dwayne K Handy
(74) *Attorney, Agent, or Firm* — Hanley, Flight & Zimmerman, LLC

(57) ABSTRACT

A system for removing liquid waste from an automated diagnostic instrument. The system comprises
(a) an accumulator having at least one inlet for waste liquids and at least one outlet for waste liquids;
(b) a vacuum sub-system connected to the accumulator, the vacuum sub-system comprising a vacuum pump; and
(c) a drain portion for removing waste liquids comprising a peristaltic pump having spring-loaded rollers.

The liquid waste from the automated diagnostic instrument is moved by a pressure differential created by the vacuum pump and the peristaltic pump having spring-loaded rollers.

22 Claims, 6 Drawing Sheets

U.S. PATENT DOCUMENTS

| | | | |
|---|---|---|---|
| 5,397,539 | A | 3/1995 | Hayashi et al. |
| 5,525,515 | A | 6/1996 | Blattner |
| 5,728,954 | A | 3/1998 | Uffenheimer |
| 5,730,938 | A | 3/1998 | Carbonari et al. |
| 5,744,099 | A | 4/1998 | Chase et al. |
| 5,789,252 | A | 8/1998 | Fujita et al. |
| 5,795,784 | A | 8/1998 | Arnquist et al. |
| 5,841,039 | A | 11/1998 | Uffenheimer |
| 5,856,194 | A | 1/1999 | Arnquist et al. |
| 5,885,530 | A | 3/1999 | Babson et al. |
| 6,096,271 | A | 8/2000 | Bogen et al. |
| 6,127,140 | A | 10/2000 | Vidakovic et al. |
| 6,267,927 | B1 | 7/2001 | Pomar Longedo et al. |
| 6,623,697 | B2 | 9/2003 | Fuerst et al. |
| 2003/0021728 | A1 | 1/2003 | Sharpe, Jr. et al. |
| 2003/0223472 | A1 | 12/2003 | Ravalico et al. |
| 2005/0005968 | A1 | 1/2005 | Berry et al. |
| 2005/0279387 | A1 | 12/2005 | Blackwell et al. |
| 2006/0263248 | A1 | 11/2006 | Gomm et al. |

FOREIGN PATENT DOCUMENTS

| | | | |
|---|---|---|---|
| EP | 0 567 093 A2 | | 10/1993 |
| EP | 0 567 093 A3 | | 10/1993 |
| EP | 0 769 547 B1 | | 4/1997 |
| EP | 0 918 221 B1 | | 5/1999 |
| EP | 1 058 826 B1 | | 12/2000 |
| GB | 2225223 A | | 5/1990 |
| JP | 02-269970 A | | 11/1990 |
| JP | 4021961 | | 1/1992 |
| JP | 05-172824 A | | 7/1993 |
| JP | 05-0293448 A | | 11/1993 |
| JP | 7294510 | | 11/1995 |
| JP | 11316235 | | 11/1999 |
| JP | 2003-075457 A | | 3/2003 |
| JP | 2003531381 | | 10/2003 |
| SU | 1222886 A | * | 11/1984 |
| WO | WO 90/08307 | | 7/1990 |
| WO | 9310454 | | 5/1993 |
| WO | WO 97/26541 | | 7/1997 |
| WO | WO 99/44031 | | 2/1999 |
| WO | WO 03/012453 A2 | | 2/2003 |
| WO | WO 03/012453 A3 | | 2/2003 |
| WO | WO 03/036273 A1 | | 5/2003 |
| WO | 2005033714 A1 | | 4/2005 |

OTHER PUBLICATIONS

International Preliminary Report on Patentability and Written Opinion of the International Searching Authority, issued by the International Bureau in connection with International Patent Application No. PCT/US2007/086216, on Jun. 23, 2009, 6 pages.

European Office Action, issued by the European Patent Office in connection with European Application No. 07 865 079.3, on Nov. 4, 2009, 3 pages.

European Office Action, issued by the European Patent Office in connection with European Application No. 07 865 079.3, on Oct. 25, 2011, 6 pages.

Summons to attend oral proceedings pursuant to Rule 115(1) EPC, issued by the European Patent Office in connection with 07 865 079.3, on Jul. 18, 2012, 8 pages.

Translation of Notice of Rejection, issued by the Japanese Patent Office in connection with Japanese Patent Application No. 2009-543024, on Jun. 26, 2012, 4 pages.

* cited by examiner

LIQUID WASTE MANAGEMENT SYSTEM

BACKGROUND OF THE INVENTION

1. Field of the Invention

This invention relates to removal of waste liquid from an automated instrument, more particularly, an automated instrument that employs a variety of liquids.

2. Discussion of the Art

The ARCHITECT® family of automated diagnostic instruments requires fluid handling systems that employ at least one sub-system for aspirating and dispensing samples and reagents, at least one sub-system for dispensing buffers, at least one sub-system for dispensing pre-trigger fluids and trigger fluids, and at least one sub-system for handling liquid waste.

Through the aspiration process, samples are moved from sample containers and assay reagents are moved from reagent bottles for dispensing into reaction vessels. In addition, wash buffer is dispensed for priming and flushing. Trigger solutions and pre-trigger solutions are also dispensed into reaction vessels.

Pipette probes, together with syringes and valves, are used to aspirate reagents from reagent bottles and dispense them into a reaction vessel. A pipette probe is used to aspirate a sample from a sample container and dispense it into a reaction vessel. Fluids are aspirated through the pipette probe(s) by a syringe and then dispensed in the same manner by reversing the direction of travel of the syringe plunger. A system of robotics positions pipette probe(s) to the appropriate bottle, container, or reaction vessel for the aspiration and dispensing process steps. The pipette probes that handle reagents are washed with wash buffer in active wash cups. The pipette probe that handles samples is washed with wash buffer in a passive wash cup. Wash zones for washing the microparticles and the inside surfaces of the reaction vessels comprise a manifold having dispensing nozzles and valves. At the wash zones, wash buffer is dispensed into reaction vessels and liquid is aspirated from reaction vessels. A waste aspiration probe is used to aspirate liquid from a reaction vessel prior to discarding the reaction vessel to solid waste.

Waste liquid in the ARCHITECT® i2000SR instrument is removed by a system of drains that relies on the principle of gravity. This system requires the use of so-called "vacuum vessels" and solenoid drain valves at each of the active wash cups and microparticle wash stations. A liquid waste management system based on that used in the ARCHITECT® i2000SR instrument is shown schematically in FIG. 1. The system 10 includes two vacuum vessels 12 and 14, vacuum vessel 12 having solenoid valves 16a and 16b associated therewith and vacuum vessel 14 having solenoid valves 18a and 18b associated therewith. A wash cup 20 is associated with the washing process for the sample probe and a wash cup 22 is associated with the washing process for the reagent probe. The waste liquid flows by gravity into a gutter system 24, which is open to the environment at several collection points, i.e., the collection point 24a from the wash cup 22 for waste liquid from the sample probe wash, the collection point 24b from the wash cup for waste liquid from the reagent probe wash, the collection point 24c from the CMIA (Chemiluminescent Microparticle Immunoassay) washer 26, the collection point 24d from the pre-trigger fluidics, the collection point 24e from the trigger fluidics, and the collection point 24f from the microparticle wash zone.

Vacuum is supplied to the ARCHITECT® i2000SR instrument for the CMIA wash process to extract wash fluid waste from the system. Vacuum is also supplied to the reagent probe wash station to dry the probe after the probe has been washed in the wash cup 22. Vacuum is used to aspirate liquid from the reaction vessels.

The vacuum system consists of an accumulator assembly 28, vacuum vessel assemblies comprising (a) the vacuum vessel 12 and solenoid valves 16a and 16b and (b) the vacuum vessel 14 and solenoid valves 18a and 18b and a vacuum pump 30 with a filter 32. The accumulator assembly 28 comprises an accumulator 28a, a vacuum switch 28b, and a liquid level sensor 28c. The vacuum system is used to supply vacuum to the active wash cup(s) 22, wash zone aspiration probes 34a, 34b, 34c and waste aspiration probe (not shown). Solenoid valves 16a and 18a are opened, allowing the vacuum to suction liquid from the reaction vessels or the wash cup 22. The liquid is drawn into a liquid separation vessel 12 and 14 where it is held until the vacuum cycle is complete. When the vacuum cycle is complete, the solenoid valve to the reaction vessel (solenoid valve 18a) or wash cup (solenoid valve 16a) close, the solenoid valves 16b and 18b to the drain open, and the liquid drains into the gutter system 24 by gravity. The liquid waste is distributed to a waste manifold 38, which can be connected to an external liquid waste floor drain 40, a waste pump (not shown), or a container (not shown). The fluid lines shown in FIG. 1 are typically made of flexible tubing, ¼-inch inside diameter for the waste removal area 44, and 1/16-inch inside diameter for the microparticle wash zone 26. The diameter(s) of such tubing is (are) readily determinable by one of ordinary skill in the art.

The liquid waste management system shown in FIG. 1 has certain drawbacks. One drawback involves excessive space requirements and, consequently, excessive cost, relative to a system that has only one wash cup, no vacuum vessel, and no gutter system. The gutter system 24 shown in FIG. 1, being open to the environment, can collect dust and other foreign objects inadvertently dropped into it. Such debris can result in a blockage of flow of liquid. Furthermore, the gutter system 24 is difficult to clean. In a system operating by gravity induced flow, the rate of flow of the waste liquid is determined by the relative height of the liquid with respect to the destination of the fluid and the flow resistance of the solenoid valves, tubing, and connections. For example, the height of the liquid in the vacuum vessels 12 and 14 is less than two inches above the solenoid valves 16b and 18b. This height differential corresponds to a pressure difference of about 0.072 psi across the solenoid valves 16b and 18b. As the pressure difference increases, the liquid can be moved in a shorter period of time and will have a wider margin for the evacuation time if the resistance to flow were to increase over time. The pressure differential available solely through the force of gravity with the ARCHITECT® i2000SR instrument is very small. Vacuum provides a much higher pressure differential and, consequently, a much higher rate of fluid flow. Accordingly, a given volume of liquid can be evacuated with in a shorter period of time. In automated analytical instruments, events are scheduled in a tight sequence. If waste liquid is not removed before the valve to the drain is scheduled to be closed, waste liquid will progressively accumulate. Higher flow rates are likely to keep the conduits for the flow of fluid cleaner. Another drawback of the system of drains based on gravity induced flow is that the laboratory drain 42 into which the waste liquid ultimately flows has to be at a lower level than the floor (not shown) on which the automated diagnostic instrument stands.

The wash cups 20 and 22 in the ARCHITECT® i2000SR instrument are used to clean the pipette probes by washing the probes after each use thereof. A passive wash cup 20 is used to wash the pipette probe that handles the sample. An active wash cup 22 is used to wash the pipette probe that handles the reagent. These wash cups 20 and 22 will not facilitate the wash protocols that are to be used on a modification of the ARCHITECT® i2000SR instrument that uses only one wash cup. This modification of the ARCHITECT® i2000SR instrument will not require a separate wash pump. Furthermore, this modification of the ARCHITECT® i2000SR instrument will be required to provide clean buffer for aspiration by the probe.

The liquid waste management system of the ARCHITECT® i2000SR instrument does not allow for the use of an on-board liquid waste container. Accordingly, removal and replacement of an on-board liquid waste container while the instrument is operating is not possible.

The liquid waste management system based on the ARCHITECT® i2000SR instrument does not have an on-board liquid waste pump. Thus, the system cannot pump the liquid waste to laboratory drains that are at a level higher than the floor on which the automated diagnostic instrument stands.

The liquid waste management system of the ARCHITECT® i2000SR instrument does not have a pressure sensor in the liquid waste outlet to sense any obstruction to the flow of liquid waste. Obstruction of the flow of liquid waste in the ARCHITECT® i2000SR instrument can lead to liquid spills, which, of course, can lead to undesirable conditions.

The vacuum pump used in the ARCHITECT® i2000SR instrument is driven by an alternating current (AC) motor at a relatively constant speed. The pump is not designed to allow for feedback control of the level of vacuum by matching the pump speed to the flow demand.

Another automated diagnostic instrument currently available is the ACCESS system, commercially available from Beckman Coulter Incorporated. The on-board liquid waste container of the ACCESS system can be removed for only a short time while the ACCESS instrument is running. Either an empty liquid waste container has to be connected immediately, or a pan must be provided to collect the liquid waste. Accordingly, it would be desirable to develop a liquid waste removal system that allows removal and replacement of an on-board liquid waste container, even while the automated diagnostic instrument is operating. It would also be desirable to develop a liquid waste removal system that allows for an optional connection to a laboratory drain. It would be further desirable to develop a liquid waste removal system for an automated diagnostic instrument that utilizes an accumulator, which can also serves as a temporary waste liquid storage container to minimize the number of components in the system, thereby reducing cost and space requirements.

SUMMARY OF THE INVENTION

In one aspect, this invention provides a system for removing liquid waste from an automated diagnostic instrument. The system comprises
(a) an accumulator having at least one inlet for waste liquids and at least one outlet for waste liquids;
(b) a vacuum sub-system connected to the accumulator, the vacuum sub-system comprising a vacuum pump; and
(c) a drain portion for removing waste liquids comprising a peristaltic pump having spring-loaded rollers.

The liquid waste from the automated diagnostic instrument is moved by means of a pressure differential created by a vacuum pump and a waste pump. The waste pump is a peristaltic pump having spring-loaded rollers. The vacuum pump moves the waste liquid to the accumulator. The waste liquid is moved from the accumulator by the peristaltic pump. The peristaltic pump increases the speed of removal of the waste liquid, reduces the number of liquid collection vessels and solenoid valves, and eliminates the need for a gravity-based system of drains, i.e., a system wherein all liquids flow from a higher level to a lower level.

The system comprises an accumulator that communicates with at least one wash station. The liquid waste from the at least one wash station is transferred to the accumulator. In one embodiment, the liquid waste removal system comprises the waste pump and a waste pump switch to transfer liquid waste to an on-board liquid waste container. The on-board liquid waste container can be removed, emptied, and replaced without interrupting the operation of the automated diagnostic instrument. The liquid waste removal system allows a sufficient amount of time, e.g., about 30 minutes, for the operation of removing and replacing the on-board liquid waste container. If the on-board liquid waste container is not replaced within the proper amount of time, the system prevents the initiation of new tests and completes only the tests already in progress.

The liquid waste management system described herein allows for the option of pumping the liquid waste directly into a laboratory drain. The laboratory drain can be located above the level of the floor, e.g., as high as 40 inches above the level of the floor.

The liquid waste management system described herein allows for feedback control of the vacuum level so that the vacuum level can be maintained within a set range during normal operation of the system.

DETAILED DESCRIPTION

As used herein, the expression "automated diagnostic instrument" means a diagnostic instrument wherein involvement of an operator in the assay processing steps is minimal. As used herein, the expression, "on-board container" means a container that fits within the confines of the automated diagnostic instrument and is capable of moving with the instrument when the instrument is moved. As used herein, the expressions "liquid waste" and "waste liquid" are used interchangeably. As used herein, the expression "active wash cup" means a wash cup that uses a separate pump to provide a flow of buffer to the wash cup for washing the exterior surface of a pipette probe for reagents; the expression "passive wash cup" means a wash cup that does not use a separate pump to provide a flow of buffer to the wash cup for washing the exterior surface of a pipette probe. When a passive wash cup is used to clean a probe, the probe is plunged into the well of the wash cup, and the buffer used to clean the interior of the probe is also used to clean the exterior surface of the probe.

Automated diagnostic instruments that are contemplated for use with the system for removing liquid waste described herein include automated diagnostic instruments, such, as, for example, ARCHITECT® automated immunoassay instruments, as modified to utilize the liquid waste removal system described herein. A representative example of such an automated diagnostic instrument that can be modified to utilize the liquid waste removal system described herein is the ARCHITECT® i2000SR instrument. This automated diagnostic instrument is described, for example, in U.S. Pat. Nos. 5,795,784 and 5,856,194, both of which are incorporated herein by reference. U.S. patent application Ser. No. 11/122, 280, filed May 4, 2005, incorporated herein by reference, describes another automated immunoassay instrument that can be adapted to use the liquid waste management system described herein. The system described in U.S. Patent Application Publication No. 2003/0223472 A1, incorporated herein by reference, can also be adapted to use the liquid waste management system described herein. In addition, the probe washing apparatus described in U.S. Patent Application Publication No. 2005/0279387 A1, incorporated herein by reference, can be adapted to use the liquid waste management system described herein.

Figure 1:
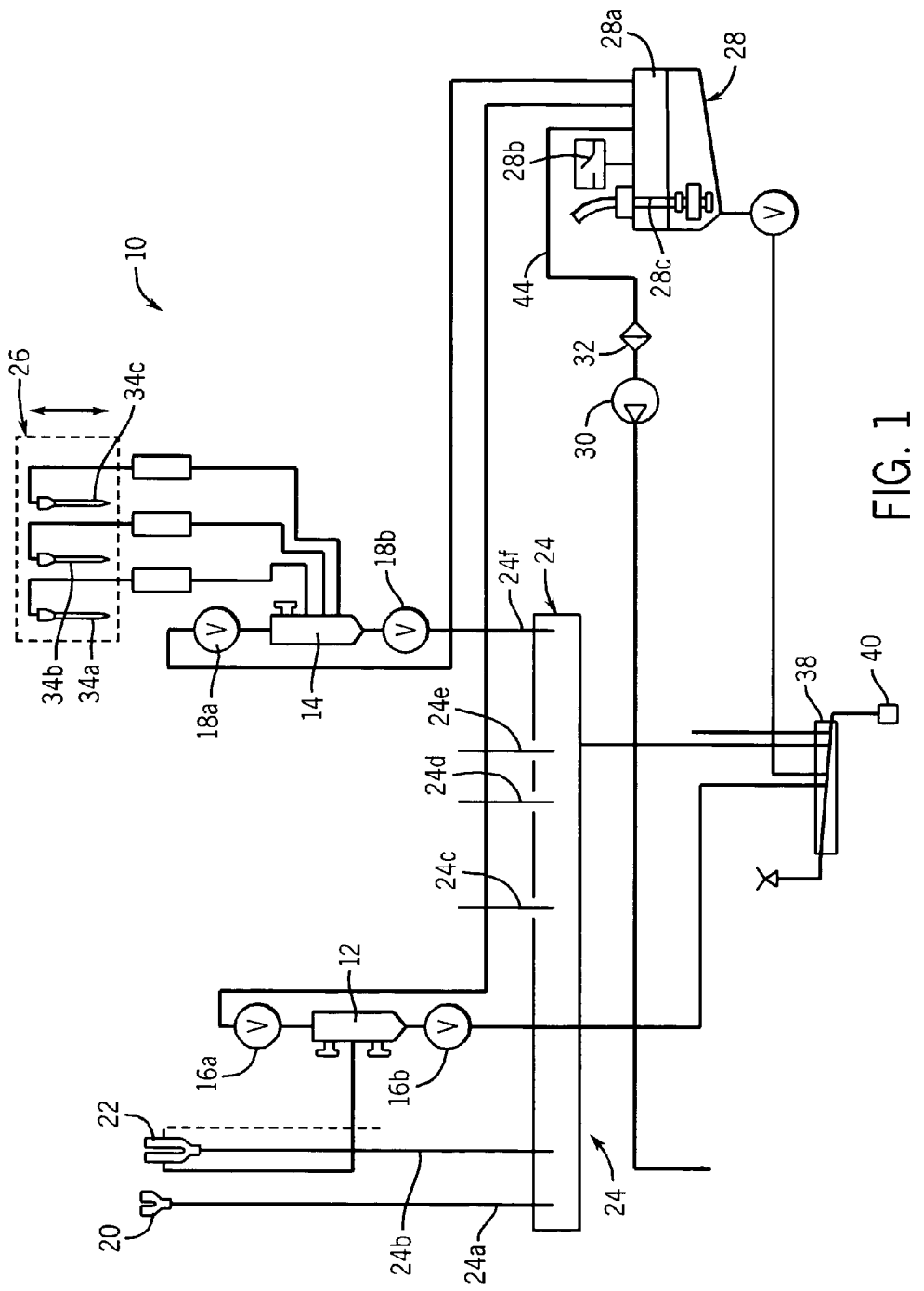
FIG. 1 is a schematic diagram illustrating a liquid waste removal system of the prior art suitable for use in an automated diagnostic instrument.
Figure 2:
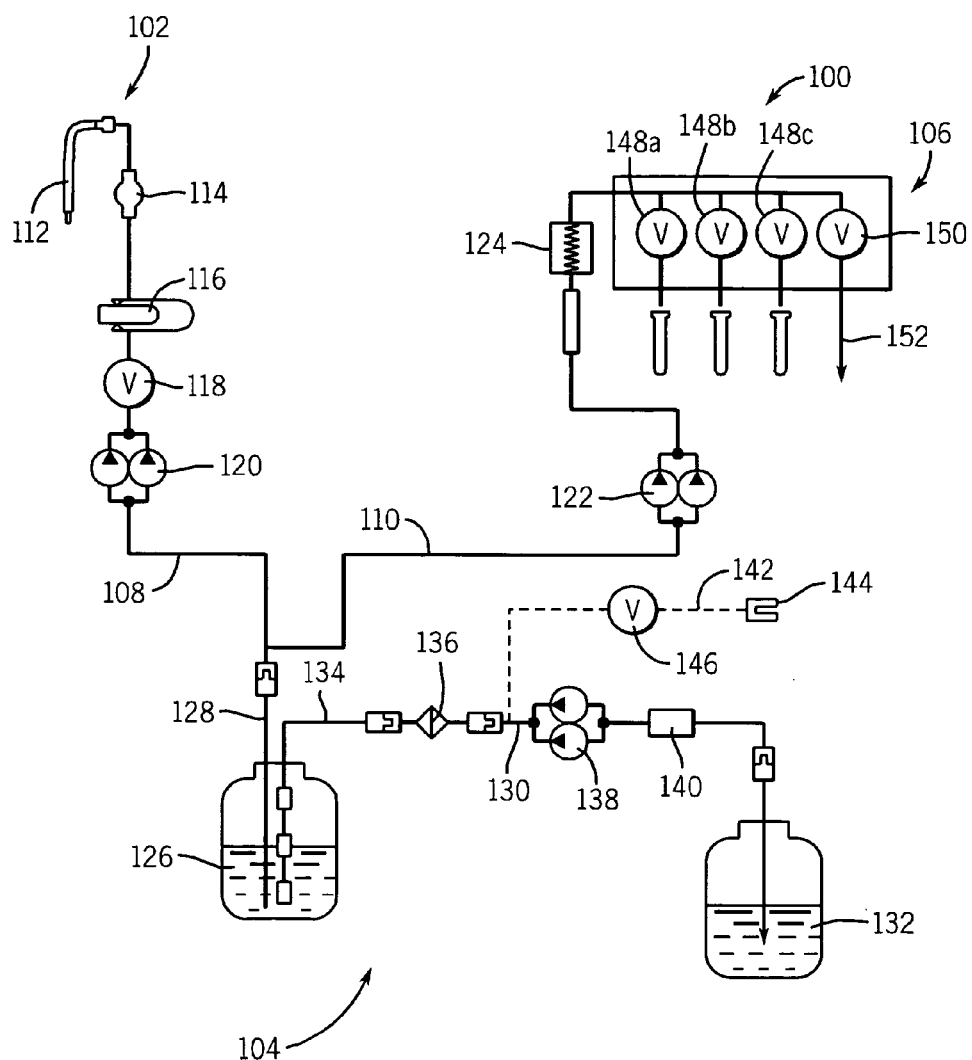
FIG. 2 is a schematic diagram illustrating a buffer dispensing sub-system suitable for use in the automated diagnostic instrument described herein.

Referring now to FIG. 2, the purposes of the buffer dispensing sub-system 100 are (a) to provide wash fluid for washing pipette probe(s), microparticles used in the assay, and reactions vessels, (b) to provide diluents for samples and reagents in assays that require dilution, and (c) to provide working fluid in the pipette circuit so that volumetric accuracy can be maintained during aspiration and dispensing of samples and reagents. The buffer dispensing sub-system 100 comprises a pipette portion 102, a buffer storage portion 104, and a wash zone portion 106.

The pipette portion 102 is connected to the buffer storage portion 104 by a fluid line 108. The wash zone portion is connected to the buffer storage portion by a fluid line 110. The fluid line 108 connecting the pipette portion 102 to the buffer storage portion 104 comprises a pipette probe 112, a pressure monitor 114, a pipette syringe 116, a syringe valve 118, and a buffer pump 120. The pipette probe 112 has the function of aspirating and dispensing the appropriate amounts of samples and reagents. The pipette probe 112 has the volumetric capacity to hold the appropriate amounts of these materials therein. A robotic mechanism (not shown) is used to properly position the pipette probe 112 in the horizontal and vertical directions. The pipette syringe 116 has the function of controlling the precise amount of liquid to be aspirated or dispensed by the pipette probe 112. The buffer pump 120 can be a positive displacement, valveless, rotary pump.

The fluid line 110 connecting the buffer storage portion 104 to the wash zone portion 106 comprises a wash zone pump 122 and a wash zone buffer heater 124. The buffer storage portion 104 comprises a buffer container 126 having an outlet 128 that leads to the fluid lines 108 and 110. The buffer storage portion 104 further comprises a fluid line 130 connecting the buffer container 126 to a buffer mixing container 132. The fluid line 130 connecting the buffer container 126 to the mixing container 132 comprises an inlet 134, a filter 136, a transfer pump 138, and a buffer transfer air detection sensor 140. The purpose of the filter 136 is to ensure that the buffer in the on-board buffer container is clean. The buffer is mixed manually in the buffer mixing container 132 by mixing concentrated buffer and deionized water. During this process, contaminants can inadvertently enter the buffer. Such contaminants can adversely affect the results of assays by causing pumps to seize and by clogging flow passages. The transfer pump 138 can be a diaphragm pump. The purpose of the buffer transfer air detection sensor 140 is to indicate when the buffer mixing container 132 is empty and for ordering the pump to stop. When all of the buffer in the buffer mixing container 132 has been transferred, the transfer pump 138 will draw in air. The buffer transfer air detection sensor 140 switches state when the fluid passing through it changes from liquid buffer to gaseous air. A fluid line 142 runs from the input 144 of an optional automatic reconstitution module (ARM) (not shown). In the fluid line 142 is a buffer inlet valve 146. The ARM enables automatic replenishment of the buffer in the buffer container 126.

The wash zone portion 106 comprises wash zone dispense valves 148a, 148b, 148c, the wash zone buffer heater 124, and a wash zone bypass valve 150. A fluid line 152 leads from the wash zone bypass valve 150 to an accumulator, which will be described in detail later. The purpose of a wash zone dispense valve, i.e., 148a, 148b, and 148c, is to is to allow the buffer to be dispensed into a particular reaction vessel at the wash zone portion 106. The purpose of the wash zone buffer heater 124 is to heat the buffer to approximately the same temperature as the contents of the reaction vessel, which are maintained at a specified temperature in the temperature controlled process path. The temperature of the buffer affects the efficacy of the washing process and needs to maintained within specified limits to obtain repeatable results. To remove air from the wash circuit, buffer is pumped through the wash circuit to the dispensing valves and is then transported to waste by opening the wash zone bypass valve 150. The amount of buffer used in this priming/flushing operation exceeds the capacity of the reaction vessels. The purpose of the wash zone bypass valve 150 is to provide an alternate path to remove this excess buffer. The small amount of air between the wash zone bypass valve 150 and the dispensing tip is removed by a separate priming step.

Figure 3:
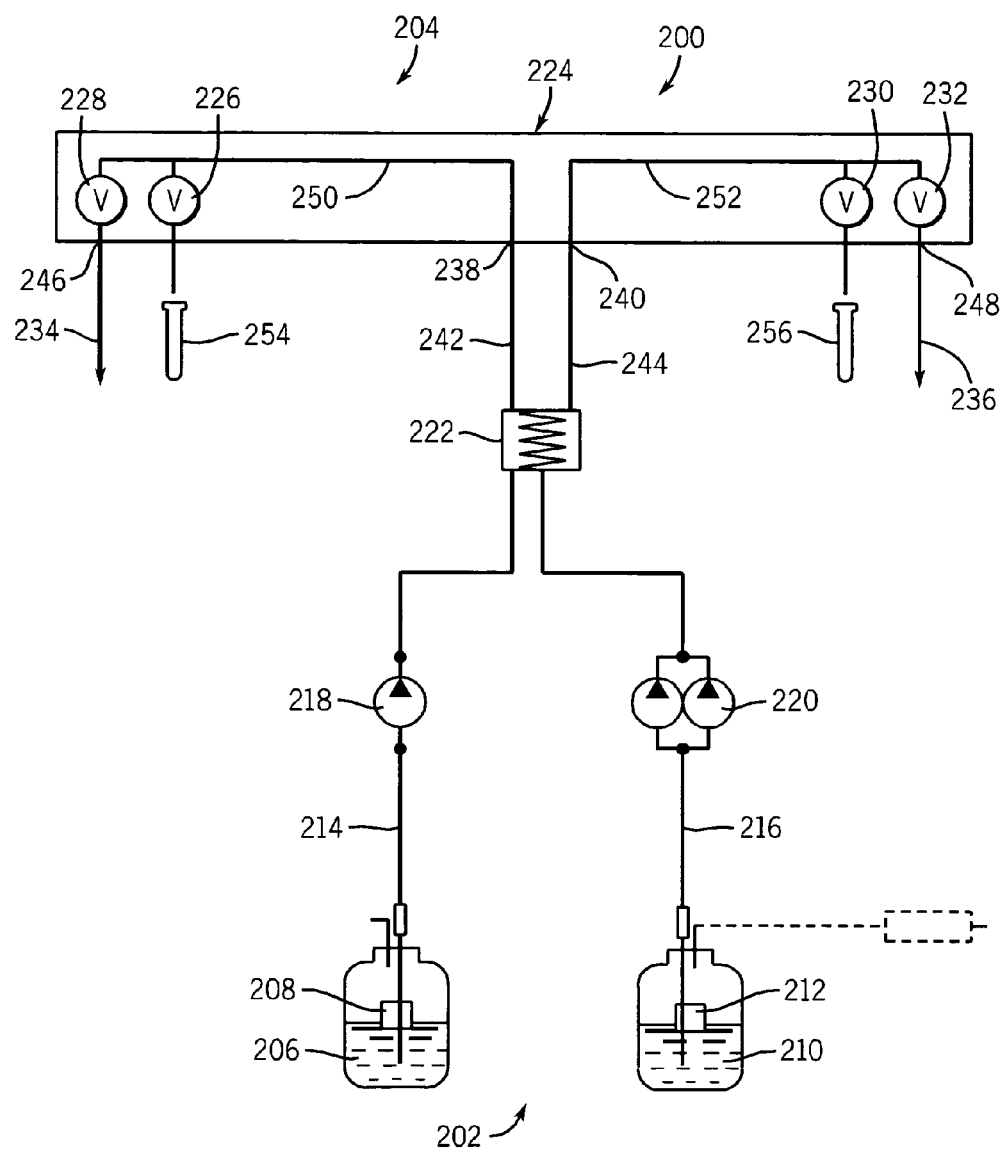
FIG. 3 is a schematic diagram illustrating a sub-system suitable for dispensing pre-trigger solution and trigger solution for use in the automated diagnostic instrument described herein.

Referring now to FIG. 3, a sub-system 200 for dispensing a pre-trigger solution and a trigger solution comprises a storage area 202 for the pre-trigger solution and the trigger solution and a dispensing portion 204 for dispensing the pre-trigger solution and the trigger solution. The pre-trigger solution and the trigger solution are used to generate light from the contents of the reaction vessel at the end of the assay processing steps. The amount of light is measured and translated into values that have clinical significance. See, for example, U.S. Pat. Nos. 5,795,784 and 5,856,194, previously incorporated herein by reference, and U.S. Pat. No. 6,127, 140, incorporated herein by reference, which further describes pre-trigger solutions and trigger solutions.

The storage area 202 comprises a container 206 for the pre-trigger solution, the container 206 being equipped with a sensor 208 for detecting the level of pre-trigger solution, and a container 210 for the trigger solution, the container 210 being equipped with a sensor 212 for detecting the level of trigger solution. A fluid line 214 connects the container 206 to the dispensing portion 204. A fluid line 216 connects the container 210 to the dispensing portion 204. The fluid line 214 comprises a pump 218 for the pre-trigger solution, and the fluid line 216 comprises a pump 220 for the trigger solution. A heater 222 for heating the pre-trigger solution and the trigger solution heats the pre-trigger solution in fluid line 214 and the trigger solution in fluid line 216. The pumps 218 and 220 can be positive displacement, valveless, rotary pumps. These pumps can be replaced by linear motion positive displacement pumps. Representative examples of pumps suitable for pumps 218 and 220 are commercially available from Fluid Metering Inc.

The dispensing portion 204 comprises a manifold 224 for the pre-trigger solution and the trigger solution. The manifold 224 has a dispense valve 226 for the pre-trigger solution and a bypass valve 228 for the pre-trigger solution. The manifold 224 further has a dispense valve 230 for the trigger solution and a bypass valve 232 for the trigger solution. The manifold itself is typically a machined part, typically made from polyvinyl chloride. The manifold 224 has entrance ports 238 and 240 for the fluid lines 242 and 244, respectively, that deliver the pre-trigger solution and the trigger solution, respectively, exit ports 246 and 248 for liquids that enter the fluid lines 234 and 236, respectively, lines 250 and 252 for the pre-trigger solution and the trigger solution, respectively, mounting and locating features (not shown) for the solenoid valves. The manifold 224 further includes the dispensing tips (not shown) through which the pre-trigger solution and the trigger solution are delivered to the reaction vessels 254 and 256, respectively. The fluid from the bypass valve 228 for the pre-trigger solution and the fluid from the bypass valve for the trigger solution is routed through fluid lines 234 and 236, respectively, through an upper waste manifold into an accumulator, which will be described in detail later. The valves 226, 228, 230, and 232 are typically two-way solenoid valves.

Figure 4:
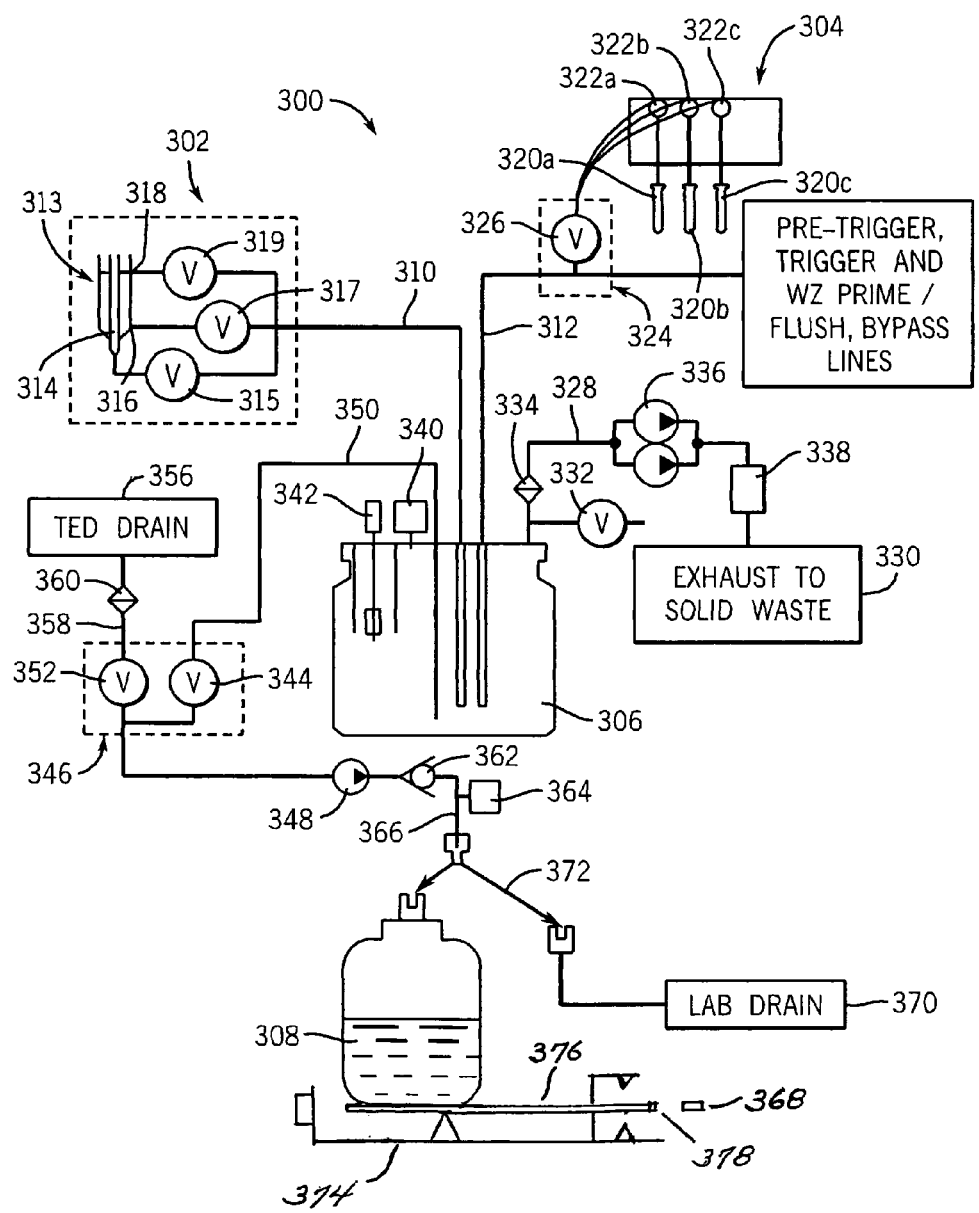
FIG. 4 is a schematic diagram illustrating a waste aspiration sub-system suitable for use in the automated diagnostic instrument described herein.

Referring now to FIG. 4, a waste aspiration sub-system 300 comprise a wash cup manifold 302, a microparticle wash station 304 (same as 106 in FIG. 2), an accumulator 306, and an on-board container 308 for liquid waste. A fluid line 310 connects the wash cup manifold 302 to the accumulator 306. A fluid line 312 connects the microparticle wash station 304 to the accumulator 306. The fluid line 312 further connects the bypass line 234 for the pre-trigger solution, the bypass line 236 for the trigger solution, the wash zone portion bypass line 152 to the accumulator 306.

The wash cup manifold 302 comprises a wash cup 313, a center well 314 for the wash cup 313, a center well drain valve 315, a waste well 316 for the wash cup 313, an outer drain valve 317, a probe drying port 318 for the wash cup 313, and a wash cup upper valve 319. The microparticle wash station 304 has three dispense nozzles (not shown) to dispense wash buffer into reaction vessels 320a, 320b, 320c and three aspiration probes 322a, 322b, 322c to aspirate the liquid from the reaction vessels 320a, 320b, 320c. Vacuum is created in the aspiration probes 322a, 322b, 322c from the upper manifold assembly 324 through a wash zone aspiration valve 326.

Opening the wash zone aspiration valve 326 connects the vacuum from the accumulator 306 to the three aspiration probes 322a, 322b, 322c so that they can aspirate liquid from the reaction vessels. The upper manifold assembly 324 is typically a component made of an acrylic polymer that has connection ports for the fittings that connect the tubing from the aspiration probes 322a, 322b, 322c, the tube from the accumulator 306, and the tubes that transport the liquids bypassing the wash zone portion 106 and the manifold 224 for the pre-trigger solution and the trigger solution.

A fluid line 328 leads from the accumulator 306 to an exhaust conduit 330 to solid waste. The fluid line 328 comprises a vacuum filter valve 332, a vacuum filter 334, a vacuum pump 336, and a muffler 338.

A vacuum pressure low sensor 340 and a sensor 342 to detect the level of liquid in the accumulator 306 serve to monitor the level of the vacuum and the level of the liquid, respectively, in the accumulator 306. A drain valve 344 for the accumulator 306, which is mounted to the lower waste manifold assembly 346, is used to connect a waste pump 348 to a drain tube 350 in the accumulator 306. The waste pump 348 is a peristaltic pump having spring-loaded rollers. A reagent cooler condensate valve 352, which is also mounted to the lower waste manifold assembly 346, is used to connect the waste pump 348 to a reagent cooler condensate reservoir (not shown). The purpose of the reagent cooler condensate reservoir (not shown) is to collect moisture that condenses in the reagent cooler (not shown). The function of the reagent cooler (not shown) is to refrigerate reagents in order to extend the useful life thereof.

The accumulator 306 suitable for use in the liquid waste management system holds reserve vacuum within set levels to provide vacuum for momentary aspiration demands. The accumulator 306 stores vacuum in the same manner that a compressed air tank stores air. The vacuum pump, designated by the reference numeral 336, can then be selected to be of a smaller size to handle the time-averaged requirement for vacuum, rather than a larger size to handle the peak demand for instantaneous vacuum, because the vacuum stored in the accumulator 306 can assist in meeting the peak demand for vacuum.

A thermoelectric device (TED) drain 356 is connected to the lower waste manifold assembly 346 by a fluid line 358. The fluid line 358 also contains a filter 360 for removing dirt and other foreign materials from the reagent cooler condensate reservoir (not shown). Such materials would adversely affect the operation of the reagent cooler condensate valve 352. A check valve 362 and a waste pump pressure switch 364 are also provided in the fluid line 366 between the waste pump 348 and the on-board container 308 for waste liquid and the optional laboratory drain 370. One purpose of the check valve 362 is to reduce pressure pulsations at the waste pump pressure switch 364 by reducing a brief reverse flow when the peristaltic waste pump has only vacuum on its inlet side. This reduction allows the waste pressure switch to be set at a relatively low pressure (5 psi nominal). Another purpose of the check valve 362 is to prevent leakage of waste liquid if the tube of the waste pump 348 fails and the waste outlet is connected to a drain that is at a higher level than the waste pump 348 (the drain can be 40 inches above floor level in certain automated diagnostic instruments). As stated previously, the waste pump 348 is a peristaltic pump having spring-loaded rollers. Such a waste pump includes a tube.

The waste pump pressure switch 364 located between the waste pump 348 and the on-board container 308 for liquid waste senses any obstruction to the flow of the waste liquid to the on-board container 308 for liquid waste or the optional laboratory drain 370 when the waste pump 348 is activated. For example, an obstruction can occur when the on-board container 308 for liquid waste is removed for emptying or when the fluid line 372 to the optional laboratory drain 370 is occluded. The check valve 362 between the lower waste manifold assembly 346 and the on-board container 308 for liquid waste is open only when the on-board container 308 for liquid waste is properly connected to the liquid waste management system. A liquid level sensor 368 is provided for the on-board container 308 for liquid waste. The on-board container 308 for liquid waste is placed in a drawer 374, which is mounted on slides. After the on-board container 308 for liquid waste is disconnected from the fluid line 366, the drawer 374 can be pulled out of the instrument to enable an operator to remove and replace the on-board container 308 for liquid waste. The liquid level sensor 368 uses the weight of a counterbalance rod 376 to set the level at which the weight of liquid in the on-board container 308 for liquid waste will cause the rod 376 to tip so that a magnet 378 at the end of the rod 376 no longer activates the liquid level sensor 368. The advantage of this arrangement is that no electrical wires are connected as an umbilical cable to the on-board container 308 for liquid waste or to the drawer 374. This arrangement also allows the system to detect if the drawer 374 has been left open, because if the drawer 374 has been left open, the magnet 378 will not be sufficiently close to the liquid level sensor 368 to activate the liquid level sensor 368.

In a typical operation of the liquid waste management system, the system aspirates twice from the probes 322a, 322b, and 322c for about three (3) seconds for each aspiration during a total interval of eighteen (18) seconds, during which interval the reaction vessels are stationary. It should be noted that the intervals mentioned herein are merely examples, and other time intervals can be used. The momentary aspiration demands referred to previously relate to the foregoing two three-second aspiration steps, during which period there is a demand for vacuum. With this extra capacity for vacuum on account of the reserve vacuum in the accumulator 306, the system can employ a smaller vacuum pump 336 without loss of performance.

The accumulator 306 can also serve as a collection container for waste liquid. The level of waste liquid in the accumulator 306 is typically maintained at less than one eighth of the total volume of the accumulator 306 by means of the waste pump 348 that periodically removes the waste liquid from the accumulator 306. The volume of the accumulator 306 has been designed so that adequate vacuum is available even if half the volume of the accumulator 306 is occupied by waste liquid. For this reason, the accumulator 306 can be used as a temporary storage container for liquid waste while the on-board container 308 for liquid waste is removed for emptying or if there is an obstruction, for a limited time, in the line 372 for connecting the liquid waste management system to the optional laboratory drain 370.

A filter 334 (e.g., a filter having a 0.2 micrometer rating) is placed on the inlet side of the vacuum pump 336 to prevent any harmful organisms from being exhausted by the vacuum pump 336. The filter 334 retains any bacteria in the atmosphere of the accumulator 306 and allows only sterile air to be drawn into the vacuum pump 336 before the air is pushed out of the exhaust of the vacuum pump 336. The filter 334 also traps any liquid droplets in the air stream. The vacuum pump 336 draws air out of the accumulator 306. This air flows through the filter 334 before it enters the vacuum pump 336. The filter 334 ensures that only sterile air is exhausted by the vacuum pump 336. Over time, liquid present in the filter 334 may increase the flow resistance of the filter 334. The increased resistance affects the response of the system and the vacuum levels during operation of the system. One approach for reducing the accumulation of liquid in the filter 334 is to periodically dry the filter by moving a large volume of ambient air through the filter 334. In FIG. 4, it can be seen that a vacuum filter valve 332 has been placed on the inlet side of the filter 334. During scheduled daily maintenance, the vacuum pump 336 is turned on and the vacuum filter valve 332 is opened so that ambient air can be drawn through the filter 334, thereby drying the filter 334. The duration of the daily maintenance is of a short period of time, e.g., about 10 minutes. The duration of daily maintenance is not affected by the addition of the filter-drying step, because the filter-drying step can be carried out in parallel with other existing daily maintenance steps.

The use of a brushless DC motor driven vacuum pump 336 and a vacuum pressure low sensor 340 allows for the use of a feedback control system that can maintain the level of vacuum within tighter limits as compared with a system in which no feedback is used. The speed (and flow rate) of the vacuum pump 336 can be increased or decreased depending on the flow demand. Reduced variability in the level of vacuum brings about a more consistent aspiration performance.

The purpose of the vacuum pump 336 is to create a vacuum that is used to aspirate liquid from the reaction vessels during assay processing. The vacuum is also used to aspirate waste liquid generated during probe washing at the wash cup manifold 302 and to dry the pipette probe (not shown in FIG. 4) after it has been washed. The vacuum pump 336 can be a dual headed diaphragm pump. The purpose of the muffler 338 is to reduce the level of audible noise caused by pulsating flow of air, which results from the vacuum pump exhaust. The outlet of the muffler 338 is placed above the solid waste container, because the exhaust from the vacuum pump 336, which contains moisture, partially condenses in the muffler 338. The purpose of the exhaust conduit 330 to solid waste is to allow the liquid from the partially condensed exhaust to drip into the solid waste container, rather than allowing the liquid to form a puddle either in the instrument or on the floor of the laboratory.

A waste pump 348 suitable for use in the liquid waste management system described herein must be able to pump liquid from the accumulator 306 even at levels of vacuum as high as 700 mm of mercury (Hg) below atmospheric pressure. The ability to pump liquid at high inlet levels of vacuum simplifies the algorithm required to determine when the waste pump 348 needs to be activated to pump the waste liquid from the accumulator 306. The algorithm determines when the waste pump 348 is to be activated to remove waste liquid from the accumulator 306. An algorithm suitable for use with the liquid waste management system described herein sums the volume of the liquid that is being directed into the accumulator 306. When the volume of liquid reaches a preset value (e.g., 225 mL), the waste pump 348 is activated for a set duration of time to pump that liquid from the accumulator 306. The controller in the system does not have to check whether the vacuum pump 336 is activated or inactivated or whether the level of vacuum is high or low. The waste pump 348 is capable of drawing the liquid from the accumulator 306 whether or not a vacuum is present.

When the particular waste pump selected is not capable of drawing liquid from the accumulator 306 if either the accumulator 306 is subject to a vacuum or if the level of vacuum in the accumulator 306 is greater than the capability of the waste pump 348, the task of the system becomes more complicated. The algorithm will have to be modified to record the total amount of the liquid in the accumulator 306. The algorithm will have to monitor the workload of the instrument to determine when the accumulator 306 is not in use and, consequently, can be maintained at atmospheric pressure for a sufficient length of time to enable liquid to be pumped from the accumulator 306.

The level of liquid in the accumulator 306 can be maintained easily within a set maximum level because the waste pump 348 can be activated without the necessity of waiting for a block of time when the level of vacuum is within the capability of the waste pump 348. The accumulator 306 is being used both as an accumulator of vacuum and as a temporary reservoir for waste liquid. For the accumulator 306 to function as an accumulator of vacuum, the accumulator 306 must have sufficient space that is not occupied by liquid. The space occupied by liquid diminishes the capacity of the accumulator 306 to provide a vacuum. In the apparatus described herein, the volumetric capacity of the accumulator 306 when empty is typically four (4) liters. Tests have shown that the combination of the vacuum pump 336 and the accumulator 306 can function adequately (i.e., provide sufficient vacuum during normal operation) if the volumetric capacity of the accumulator 306 is reduced to two (2) liters. Accordingly, the set maximum level for the waste liquid being collected in the accumulator can be set to two (2) liters. A liquid level sensor 342 in the accumulator 306 detects waste liquid at the set maximum level and signals the instrument controller to cease operations. Under normal operating conditions, this set maximum level for the waste liquid is never reached because the waste pump 348 removes the liquid as soon as, for example, 225 mL of liquid is collected. The waste pump 348 described herein is capable of pumping liquid from the accumulator 306 even at a vacuum level of 700 mm Hg below atmospheric pressure. Every type of pump, such as, for example, a diaphragm pump, a bellows pump, a sliding piston pump, or a peristaltic pump of a design not described herein, will have a certain limiting vacuum level at which it will be able to function at a certain operating speed. The actual value of the limiting vacuum level will depend on the particular design of the pump. For example, a particular pump may be capable of pumping liquid only if the level of vacuum ranges from 0 mm Hg to 400 mm Hg below atmospheric pressure. If such a pump were used in the apparatus described herein, that is, wherein the level of vacuum can range from 400 mm Hg to more than 700 mm Hg below atmospheric pressure, the system will have to wait for a block of time when the level of vacuum ranges from 0 mm Hg to 400 mm Hg below atmospheric pressure or when the vacuum pump 336 is inactivated and the accumulator 306 is at atmospheric pressure.

A type of waste pump 348 particularly suitable for use in the system described herein is a peristaltic pump having spring-loaded rollers and a tube having a relatively thick wall. The spring-loaded rollers compensate for any changes in the resilience or shape of the rubber/polymeric tube of the peristaltic pump. A representative example of a peristaltic pump suitable for use in this invention is commercially available from Shurflo (series 300).

Figure 6:
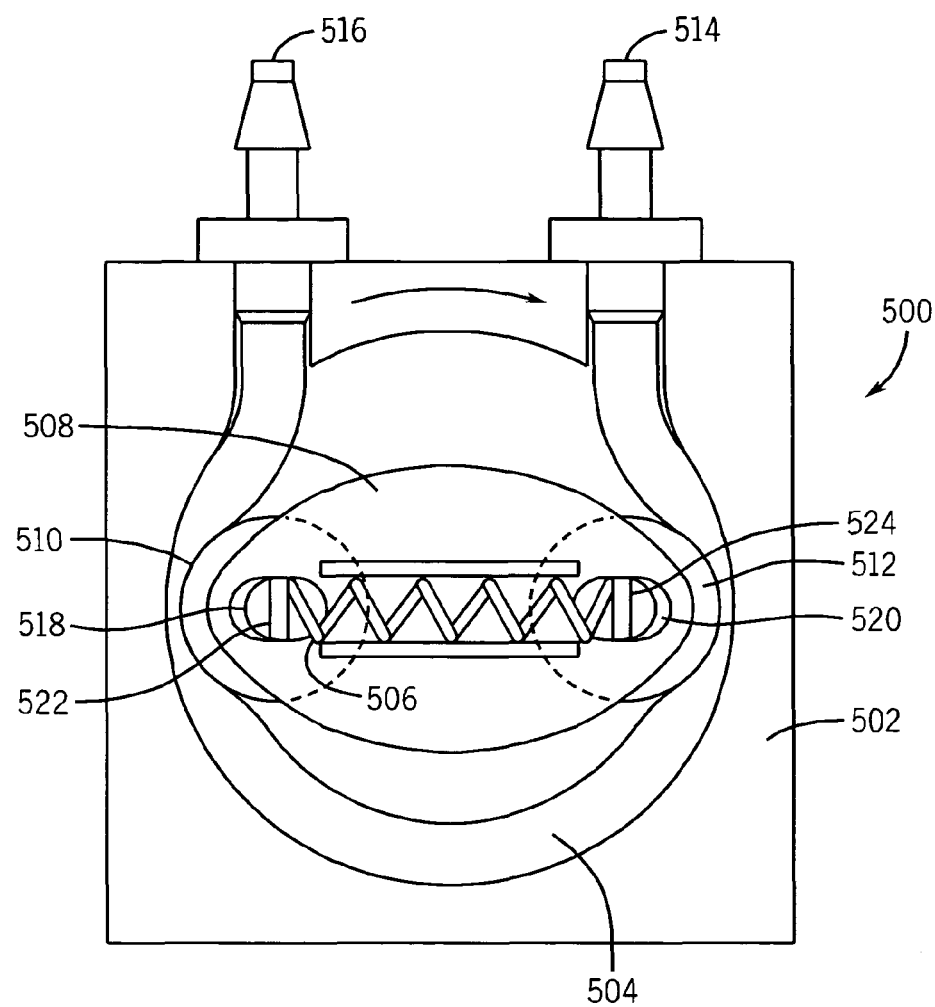
FIG. 6 is a schematic diagram illustrating a peristaltic pump suitable for use in the automated diagnostic instrument described herein.

Referring now to FIG. 6, a peristaltic pump 500 having spring-loaded rollers comprises a housing 502, a tube 504, a spring 506, a rotor 508, a first roller 510, and a second roller 512. The tube 504 has an inlet 514 and an outlet 516. The first roller 510 has an axle 518. The second roller has an axle 520. The spring 506 has a first end 522 attached to the axle 518 and a second end 524 attached to the axle 520. The rotor 508 rotates the rollers 510 and 512, which travel around the housing 502 pinching the tube 504 along the way, whereby waste liquid is carried in the portion of the tube 504 between the rollers 510 and 512. Such a pump has been found to be particularly useful because it has been found to be difficult to remove liquid from the accumulator 306 when the pressure above the surface of the waste liquid is extremely low, e.g., at least about 700 mm of mercury below atmospheric pressure. Because of this pre-existing low level of pressure, there is a great need to reduce the pressure even more at the outlet 350 of the accumulator 306 to create a pressure differential sufficient to induce the flow of the liquid from the accumulator 306.

The material of tube 504 can be a blend of EPDM and polypropylene (e.g., "NORPRENE", commercially available from Saint-Gobain Performance Plastics Corporation, Akron, Ohio). This material provides adequate chemical resistance to the waste liquids being handled. This material also has the mechanical properties needed for the pumping process. The hardness of the material for the tubing 504 is preferably greater than 60 Shore A in order to resist the effect of the vacuum, which tends to induce the tube to collapse. This material has sufficient durability with respect to tearing and sufficient resistance to taking a permanent set during the continual pinching and unpinching action of the spring-loaded rollers 510 and 512 of the peristaltic pump 500. The lower the ratio of the inside diameter of the tube 504 to the outside diameter of the tube 504, the better the ability of the tube 504 to maintain the effectiveness of the pump 500 when the pressure at the inlet 514 is at about 700 mm Hg. The diameter of the rollers 510 and 512 and the extent of lubrication affect the life of the tube 504. It is important to provide the spring-load on the rollers 510 and 512 to compensate for any creep in the material of the tube 504 and to maintain an adequate seal at the pinch point. It was observed that those peristaltic pumps that used fixed rollers to provide a predetermined level of pinching usually failed to adequately seal the pinch point after an inordinately low number of hours because of a combination of material creep and wear. The particular number of spring-loaded rollers is not important. Furthermore, a pulsatile flow of the waste liquid is acceptable. (In some peristaltic pump applications for which a steady flow is desirable, the pump is equipped with more rollers to try to approximate a steady flow.)

It has been found that a peristaltic pump having spring-loaded rollers can induce flow of liquid out of the outlet 350 of the accumulator 306 when the pressure over the surface of the waste liquid in the accumulator 306 is extremely low, such as, for example, 700 mm Hg below atmospheric pressure.

Figure 5:
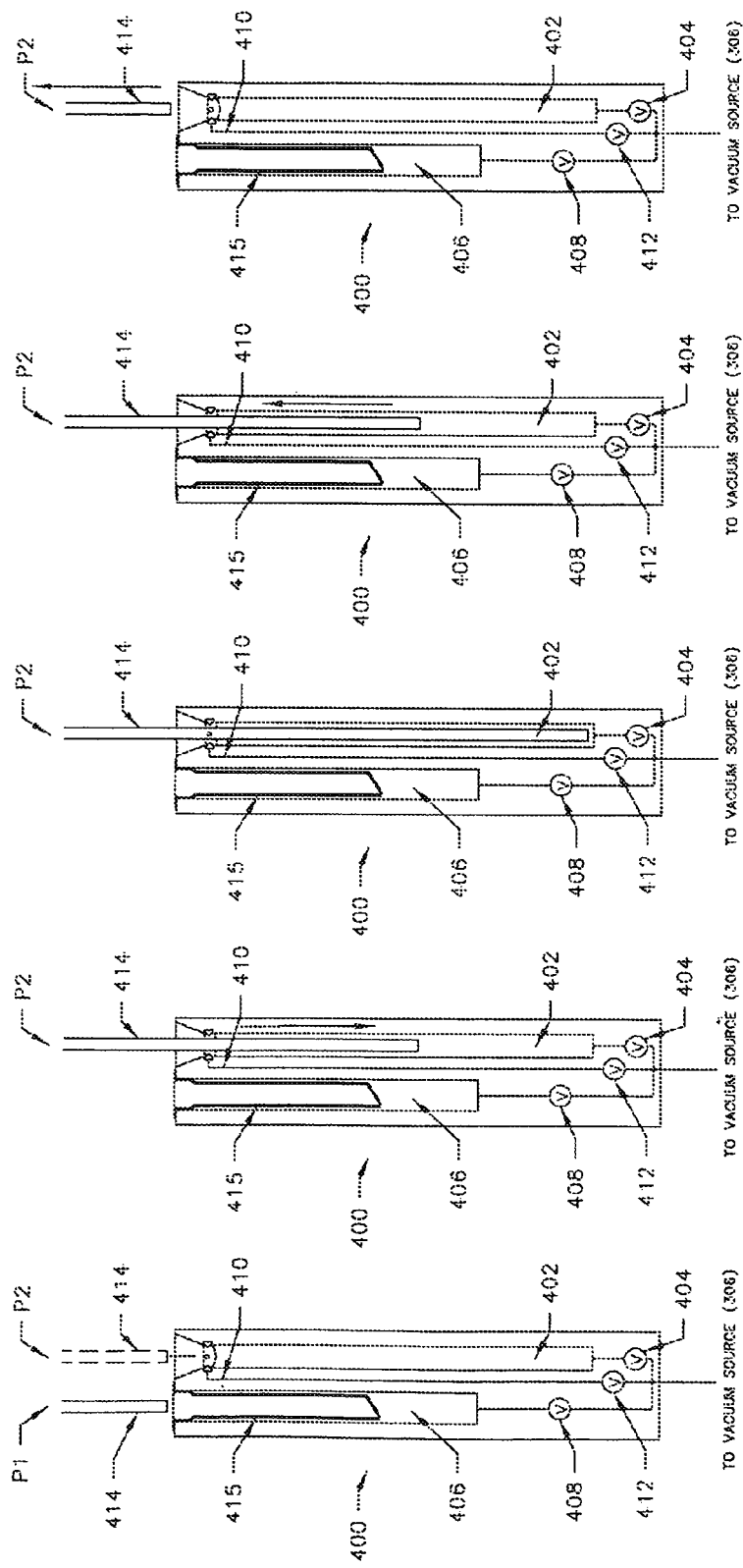
FIGS. 5A through 5E, inclusive, are schematic diagrams illustrating a wash cycle for cleaning a pipette probe used to handle samples and reagents.

The principle of operation of the wash cup is shown in FIGS. 5A through 5E, inclusive. Referring now to FIGS. 5A through 5E, a wash cup 400 (same as 313 in FIG. 4) comprises a center well 402 (same as 314 in FIG. 4) having a center well drain valve 404 (same as 315 in FIG. 4), a waste well 406 (same as 316 in FIG. 4) having an outer well drain valve 408 (same as 317 in FIG. 4), and a probe drying port 410 (same as 318 in FIG. 4) having a wash cup upper valve 412 (same as 319 in FIG. 4) capable of being connected to a vacuum. The wash cup upper valve 412 is used to provide vacuum to aspirate the liquid being pumped through the pipette probe 414 as the pipette probe 414 is being washed in the wash well 402. This vacuum also removes excess moisture from the surface of the probe (i.e., dries the probe) as the probe exits the wash well 402. In FIG. 5A, a pipette probe 414 is shown discharging any residual waste present in the pipette probe 414 and additional wash buffer at a first position P1 over the waste well 406. After the completion of this step, the pipette probe 414 is moved to a second position P2 above the wash well 402. In FIG. 5B, the pipette probe 414 descends to provide a washing of the exterior surface of the pipette probe 414. In FIG. 5C, buffer is aspirated and washing of the interior surface of the pipette probe 414 is begun. In FIG. 5D, the pipette probe 414 ascends while the interior surface thereof is being washed and the exterior surface thereof is being dried by vacuum applied at the probe drying port 410. In FIG. 5E, the wash is complete. The wash cup 400 used in the liquid waste management system is further described in U.S. Patent Publication No. 2005/0279387 A1, previously incorporated herein by reference. A single wash cup 400 can be used for washing the pipette probe 414. This wash cup 400 does not require the use of an additional pump to wash the exterior surface of the pipette probe 414. The wash cup can use a baffle 415 in the waste well 406 to reduce the level of noise emitted from the suction of the liquid and air in the waste well 406 when the valve 408 is opened. The baffle can be removed form the waste well 406 for cleaning.

Fluid lines mentioned herein, such as, for example, those represented by reference numerals 108, 110, 130, 142, 152, 214, 216, 234, 236, 242, 244, 250, 252, 310, 312, 328, 358, 366, and 372, are typically made of flexible silicone tubing.

The diameter(s) of such tubing for a particular purpose is (are) readily determinable by one of ordinary skill in the art.

There are numerous sources of waste liquid in an automated diagnostic instrument. One source of waste liquid is liquid for priming the instrument. The liquid dispensing pumps must be primed before use by pumping sufficient liquid to fill tubing and pumps and to remove any bubbles of gas, e.g., air, in the liquid flow circuit. Excess priming liquid in the pipette circuit is dispensed by the pipette probe 414 into the waste well 406 (same as 316 of FIG. 4) or of the wash cup 400 (same as 313 of FIG. 4). This liquid is aspirated into the accumulator 306 by opening the wash cup outer well drain valve 408 (same as 317 of FIG. 4). The excess liquid generated during the priming of the wash zone pump 128 is pumped into the accumulator 306 by opening the wash zone bypass valve 138 during the priming process. The liquid generated by during the priming of the pump 214 for the pre-trigger solution and the pump 216 for the trigger solution are pumped directly into the accumulator 306 by opening the corresponding bypass valves 224 and 228, respectively.

Another source of waste liquid is the liquid aspirated from the reaction vessels 320a, 320b, 320c in the microparticle wash station 304. Vacuum is applied to the three wash zone aspiration probes 322a, 322b, 322c by opening the wash zone aspiration valve 326, and the wash zone aspiration probes 322a, 322b, 322c aspirate the liquid in the reaction vessels 320a, 320b, 320c as the wash zone aspiration probes 320a, 320b, 320c are lowered into the reaction vessels 320a, 320b, 320c. The liquid from the microparticle wash station 304 is collected in the accumulator 306.

A third source of waste liquid is the pipette probe 414, which is part of the pipette circuit. The pipette probe 414 must be washed and dried after each use in order to be used for aspirating and dispensing sample or reagent. The washing is carried out in the wash cup 400 and the liquid generated during this process is aspirated into the accumulator 306 by opening the upper valve 412 (same as 319 in FIG. 4) of the wash cup 400 (same as 313 in FIG. 4) and the outer well drain valve 408 (same as 317 in FIG. 4) of the wash cup 400 (same as 313 in FIG. 4) at the appropriate times during the wash cycle. The center well drain valve 404 (same as 315 in FIG. 4) of the wash cup 400 (same as 313 in FIG. 4) is used to drain liquid in the center well 404 (same as 315 in FIG. 4) of the wash cup 400 (same as 313 in FIG. 4).

A fourth source of waste liquid is the moisture in the air in the reagent cooler (not shown). This moisture can condense and collect as water inside the reagent cooler. The waste pump 348 periodically collects the condensate in the reagent cooler by opening the reagent cooler condensate valve 352 to enable the condensate to be pumped directly to the on-board liquid waste container 308 or to the laboratory drain 370.

A fifth source of waste liquid is the assay itself. In the final steps of a typical assay, about 100 microliters of pre-trigger solution and about 400 microliters of trigger solution are typically dispensed into the reaction vessels 322a, 322b, 322c. These small amounts of liquids are also deemed waste liquid, but these liquids remain inside the reaction vessels 320a, 320b, 320c as they are dropped into the waste container for reaction vessels (not shown). The liquid waste generated by the assay itself is not handled by the liquid waste management system described herein.

The ACCESS system, commercially available from Beckman Coulter Incorporated, does not use vacuum to aspirate liquid waste from reaction vessels. The ACCESS system uses three peristaltic pumps connected to the three aspiration probes to aspirate the liquid waste from reaction vessels. The ACCESS system uses an active wash cup for washing the probe. This operation requires the flow of the wash fluid by means of an additional pump, such as, for example, a wash pump having a distribution valve. The on-board liquid waste container of the ACCESS system can be removed for only a short time while the ACCESS instrument is running. Either an empty liquid waste container has to be connected immediately, or a pan must be provided to collect the liquid waste. The glass vacuum/waste bottle has a relatively small volume compared with the volume of the accumulator described herein. The glass vacuum/waste bottle is a relatively small bottle (about 250 mL capacity) that can perform some of the same functions as the accumulator 306 (typically 4 liters capacity) in the system described herein. The glass vacuum/waste bottle is used to provide vacuum to the active wash cup. The glass vacuum/waste bottle is not used to provide vacuum for aspirating liquid from the reaction vessels. The system uses a peristaltic pump for that function. These pumps pump the waste liquid into the glass vacuum/waste bottle. Two other peristaltic pumps pump the liquid from the glass vacuum/waste bottle and into the on-board container for liquid waste. The glass vacuum/waste bottle does not have sufficient capacity to act as a temporary liquid waste storage bottle to allow the on-board container for liquid waste to be removed while the instrument is running (as can be done in the system described herein).

The ACCESS system has no liquid level sensor to detect any malfunction in the peristaltic pump that evacuates liquids from the system. The ACCESS system has no waste pump pressure switch to indicate whether the flow of waste liquid is obstructed.

The waste pump and the aspiration pumps of the ACCESS system are all peristaltic pumps driven by the same motor. It is not possible to cease pumping waste liquid while the system is in operation, because the motor must be operating during the aspiration operation. The waste pump of the ACCESS system is most likely not capable of removing liquid from the glass waste bottle if the level of vacuum is high. The ACCESS system can possibly be configured for feedback control of the vacuum level, because the ACCESS system uses a DC motor to drive the vacuum pump and has a vacuum sensor that can be used for feedback. However, feedback is not suggested to maintain the vacuum between tight limits, because the vacuum pump is used only to aspirate the waste liquid from the active wash cup. The vacuum pump is present because it increases the speed of the flow of waste liquid (as compared with the force of gravity alone) and it assists the drying of the probe after the wash. Because there is no means for drying the filter on the exhaust of the vacuum pump/waste bottle, the size and the configuration of the filter must be selected so that the liquid collected in the filter does not prematurely clog the filter. If the filter is not replaced when it is clogged, a positive pressure may build up in the waste bottle, and the operator may have to cautiously release that pressure when emptying the waste bottle.

The novel system described herein requires only one accumulator 306, which also serves as a temporary waste liquid storage container. The accumulator 306 minimizes the number of components in the system, thereby reducing cost and space requirements.

The novel system described herein allows removal and replacement of an on-board liquid waste container 308, even while the automated diagnostic instrument is operating. The novel system described herein allows a reasonable length of time (e.g., at least about 30 minutes) for the on-board liquid waste container 308 to be removed and replaced. If the on-board liquid waste container 308 is not replaced within the proper amount of time, the system prevents the initiation of new tests and completes only the tests already in progress.

The novel system described herein allows for an optional connection to a laboratory drain. The on-board waste pump 348 is capable of pumping the waste to a drain that is positioned at a level higher than that of the automated diagnostic instrument.

The novel system described herein employs a waste pump pressure switch 364 to sense any obstruction to the flow of waste liquid. This switch 364 alerts the operator of the instrument so that the obstruction can be removed. The novel system described herein system uses a wash cup that does not require an additional pump to wash the exterior surface of the pipette probe 414. The wash cup 400 (same as 313 in FIG. 4) also allows special wash protocols that increase the efficiency of the wash. The novel system reduces acoustical noise emitted from the wash cup 400 (same as 313 in FIG. 4) by means of a baffle. This baffle, access to which facilitates the cleaning thereof, also functions to trap any waste that can potentially clog the drain passages. All waste liquid movement is facilitated by using either a vacuum pump or a waste pump rather than by relying upon gravity alone. The rate of flow of waste liquid is higher than that of a gravity-based system, thereby facilitating the removal of components in the flow path.

The novel system described herein has a means for drying the filter 334 that is used to filter the exhaust from the vacuum pump 348. This drying function extends the useful life of the filter 334. The novel system described herein provides for feedback control of the level of vacuum in the accumulator 306 so that the level of vacuum can be maintained within a smaller range. Lower variability in the level of vacuum will lead to lower variability during aspiration of waste liquid from the reaction vessels.

The novel system described herein uses a waste pump 348 that is capable of extracting waste liquid from the accumulator 306 even at relatively high levels of vacuum (about 700 mm Hg below atmospheric pressure). The waste pump 348 allows the system to maintain the level of liquid in the accumulator 306 within a set maximum level regardless of the level of vacuum required by the system during normal operations. The system does not have to pause until the level of vacuum is sufficiently low (i.e., atmospheric pressure is relatively high) for the waste pump 348 to be effective. This capability simplifies the algorithm that controls the operation of the waste pump.

The wash protocols suitable for use with the automated diagnostic instrument described herein do not require an additional pump for an active wash cup. The wash protocols enable control of cross contamination of samples and reagents resulting from inadequate washing of the pipette probe as at least as well as does the i2000SR system. The wash protocols require less wash buffer for equivalent performance.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A system for removing waste liquids from an automated diagnostic instrument, said system comprising:
   an accumulator having an inlet for a waste liquid and an outlet for the waste liquid;
   a vacuum sub-system connected to the accumulator, said vacuum sub-system comprising a vacuum pump and a control system to sense the level of vacuum and to change the speed of the vacuum pump, said control system allowing for feedback control of the level of vacuum to maintain the level of vacuum within a set range; and
   a drain portion for removing the waste liquid, the drain portion comprising a peristaltic pump having spring-loaded rollers.

2. The system of claim 1, wherein said accumulator is to communicate with a wash station.

3. The system of claim 1, wherein the peristaltic pump is to transfer liquid waste to an on-board container liquid waste.

4. The system of claim 3, wherein the on-board container for liquid waste can be removed, emptied, and replaced without interrupting the operation of the automated diagnostic instrument.

5. The system of claim 4, wherein, if the on-board container for liquid waste is not replaced within a threshold period of time, the system prevents initiation of new tests and completes only tests already in progress.

6. The system of claim 3, further including a check valve between the peristaltic pump and the on-board container for liquid waste.

7. The system of claim 3, wherein the on-board container for liquid waste is to utilize a liquid level sensor.

8. The system of claim 1, wherein liquid waste is moved by a pressure differential created by the vacuum pump and the peristaltic pump having spring-loaded rollers.

9. The system of claim 1, wherein the liquid waste is pumped directly into a drain of a laboratory.

10. The system of claim 1, wherein the drain is located above the level of a floor.

11. The system of claim 1, wherein the inlet for the accumulator is to receive the waste liquid from at least two of a first reaction vessel, a second reaction vessel, a pipette probe, or a reagent cooler.

12. The system of claim 1, wherein the inlet for the accumulator is to receive the waste liquid from a reaction vessel.

13. The system of claim 1, wherein the inlet for the accumulator is to receive the waste liquid from a pipette probe.

14. The system of claim 1, wherein the inlet for the accumulator is to receive the waste liquid from a reagent cooler.

15. The system of claim 1, wherein the accumulator is to utilize a liquid level sensor and a vacuum pressure sensor.

16. The system of claim 1, further including a waste pump pressure switch.

17. The system of claim 1, further including a reagent cooler condensate reservoir.

18. The system of claim 1, wherein the vacuum sub-system further comprises a filter and a muffler.

19. The system of claim 1, wherein a first level of a drain can be up to about 40 inches above a second level of a floor upon which the instrument stands.

20. The system of claim 1, wherein a source of waste for the system includes a fluid used to prime the automated diagnostic instrument.

21. The system of claim 1, wherein the inlet of the accumulator is fluidly coupled to a wash station of the automated diagnostic instrument.

22. The system claim 21, wherein the automated diagnostic instrument further comprises a buffer dispensing system, a pre-trigger solution dispensing system, and a trigger solution dispensing system, and the accumulator is to receive waste from one or more of the buffer dispensing system, the pre-trigger solution dispensing system or the trigger solution dispensing system.

* * * * *

UNITED STATES PATENT AND TRADEMARK OFFICE
CERTIFICATE OF CORRECTION

PATENT NO.        : 8,449,839 B2  Page 1 of 1
APPLICATION NO.   : 11/644086
DATED             : May 28, 2013
INVENTOR(S)       : Ganesh Rajagopal et al.

It is certified that error appears in the above-identified patent and that said Letters Patent is hereby corrected as shown below:

In the Claims:

Col. 16, lines 10-11 should read,

3. The system of claim 1, wherein the peristaltic pump is to transfer liquid waste to an on-board container for liquid waste.

Signed and Sealed this
Twenty-second Day of April, 2014

Michelle K. Lee
*Deputy Director of the United States Patent and Trademark Office*